US009233765B2

(12) United States Patent
Gibson et al.

(10) Patent No.: US 9,233,765 B2
(45) Date of Patent: Jan. 12, 2016

(54) MULTI-DIMENSIONAL DAMAGE DETECTION

(75) Inventors: Tracy L. Gibson, Melbourne, FL (US); Martha K. Williams, Titusville, FL (US); Mark E. Lewis, Merritt Island, FL (US); Luke B. Roberson, Titusville, FL (US); Sarah J. Snyder, Terre Haute, IN (US); Pedro J. Medelius, Merritt Island, FL (US); Steven L. Parks, Rockledge, FL (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 668 days.

(21) Appl. No.: 13/495,862

(22) Filed: Jun. 13, 2012

(65) Prior Publication Data
US 2012/0318925 A1 Dec. 20, 2012

Related U.S. Application Data

(60) Provisional application No. 61/497,631, filed on Jun. 16, 2011.

(51) Int. Cl.
*B64G 1/52* (2006.01)
*B64G 1/22* (2006.01)

(52) U.S. Cl.
CPC ............ *B64G 1/52* (2013.01); *B64G 2001/224* (2013.01)

(58) Field of Classification Search
CPC .......................... B64G 1/52; B64G 2001/224
USPC ...................................... 244/158.3
See application file for complete search history.

(56) References Cited

U.S. PATENT DOCUMENTS

| 6,370,964 | B1* | 4/2002 | Chang et al. ............. 73/862.046 |
| 6,768,312 | B2 | 7/2004 | Sun et al. |
| 7,277,822 | B2* | 10/2007 | Blemel ........................ 702/183 |
| 7,413,919 | B2 | 8/2008 | Qing et al. |
| 7,676,775 | B2* | 3/2010 | Chen et al. .................... 716/136 |
| 2004/0238686 | A1 | 12/2004 | Sneed |
| 2005/0284232 | A1* | 12/2005 | Rice ............................... 73/762 |

(Continued)

FOREIGN PATENT DOCUMENTS

JP 2009006497 A 1/2009

OTHER PUBLICATIONS

M. Kokot, Damage Identification in Electrical Network for Structural Health Monitoring, Ph.D. Dissertation, 2011, pp. 1-102.

(Continued)

*Primary Examiner* — Justin Benedik
(74) *Attorney, Agent, or Firm* — Michelle L. Ford; B. Delano Jordan (57) ABSTRACT

Methods and systems may provide for a structure having a plurality of interconnected panels, wherein each panel has a plurality of detection layers separated from one another by one or more non-detection layers. The plurality of detection layers may form a grid of conductive traces. Additionally, a monitor may be coupled to each grid of conductive traces, wherein the monitor is configured to detect damage to the plurality of interconnected panels in response to an electrical property change with respect to one or more of the conductive traces. In one example, the structure is part of an inflatable space platform such as a spacecraft or habitat.

9 Claims, 5 Drawing Sheets

(56) References Cited

U.S. PATENT DOCUMENTS

| | | |
|---|---|---|
| 2006/0053534 A1 | 3/2006 | Mullen |
| 2006/0082366 A1 | 4/2006 | Goldfine et al. |
| 2006/0283266 A1 | 12/2006 | Qing et al. |
| 2007/0183110 A1* | 8/2007 | Woodard et al. ............... 361/103 |
| 2008/0075934 A1* | 3/2008 | Barlow et al. .................. 428/199 |
| 2010/0161244 A1 | 6/2010 | Ghoshal et al. |
| 2011/0107843 A1 | 5/2011 | Hucker et al. |
| 2012/0111599 A1* | 5/2012 | Roberson et al. ............. 174/107 |
| 2012/0188078 A1 | 7/2012 | Soles et al. |

OTHER PUBLICATIONS

E. Brandon, Damage Detection and Self-Repair in Inflatable/Deployable Structures, NASA Tech Briefs, Mar. 2009, vol. 33, No. 3, p. 19.

* cited by examiner

MULTI-DIMENSIONAL DAMAGE DETECTION

CROSS-REFERENCE TO RELATED APPLICATIONS

This application claims the benefit of priority under 35 U.S.C. §119(e) from U.S. Provisional Patent Application Ser. No. 61/497,631 filed on Jun. 16, 2011, the contents of which are incorporated herein by reference.

ORIGIN OF THE INVENTION

The invention described herein was made in the performance of work under a NASA contract and by employees of the United States Government and is subject to the provisions of Public Law 96-517 (35 U.S.C. §202), and may be manufactured and used by or for the Government for governmental purposes without the payment of any royalties thereon or therefore.

BACKGROUND OF THE INVENTION

1. Technical Field

Embodiments of the invention generally relate to damage detection. More particularly, embodiments relate to the use of a grid of conductive traces to detect damage to platforms such as inflatable spacecraft structures, rigid habitation structures, other terrestrial inflatable structures, and composites.

2. Discussion

Early versions of inflatable structures intended for use in outer space and habitation often relied upon the use of thin films to produce the structure's outer skin. More recently, approaches to creating such inflatable structures utilize a multilayer approach, with relatively thin layers separated by thicker, more robust layers, providing a layered composite structure with significantly improved damage resistance. Even though such composite structures are more robust, they are susceptible to penetration damage from micrometeorites and other space debris.

During launch and landing operations, plume ejecta can be a significant source of damaging debris. Currently, the method for determining damage to inflatable structures utilizes differential pressure systems, which tend to work better if damage causes an actual leak. However, if the damage is relatively minor, it is more difficult to determine the extent of the damage. Minor damage can lead to more significant damage if undetected and not addressed as soon as possible.

In an effort to detect such damage, very thin wires or conductive traces or fibers may be embedded into the composite material. Such systems can be difficult to fabricate, however, and may not be easy to connect together at the system level. The present invention provides new and novel methods, systems, and apparatus for use in damage detection applications.

BRIEF DESCRIPTION OF THE DRAWINGS

The various advantages of the embodiments of the present invention will become apparent to one of ordinary skill in the art by reading the following specification and appended claims, and by referencing the following drawings, in which:

DETAILED DESCRIPTION OF THE INVENTION

Embodiments of the present invention may provide a method of detecting damages to surfaces. For example, the exterior structure of an inflatable space platform such as a spacecraft or habitat located in outer space. Damage caused by impacts of foreign objects, e.g., micrometeorites, can easily rupture the shell of the inflatable or habitation structure, causing loss of critical hardware and/or life of the crew. While not all impacts will have a catastrophic result, it can be advantageous to identify and locate areas of the exterior shell that have been damaged by impact so that repairs (or other provisions) can be made to reduce the probability of shell rupture and ultimate failure. Embodiments of the present invention involve a system that may provide real-time data regarding the health of the inflatable shell of a structure, specifically including data related to the location and depth of any impact damage. Other embodiments include detecting damage to aircraft, spacecraft, composite materials, and textiles. Still further embodiments involve detecting damage to interior surfaces, non-inflatable structures, and other terrestrial inflatable structures such as military shelters.

Embodiments of the present invention can also provide a multi-dimensional damage detection system that identifies both the precise location and extent of damage to an inflatable structure. Incorporated into the embodiments may be related technology of detecting damage to thin films, including new methods of fabricating and testing new versions of conductive materials in thin-film layers that may be utilized in external structures, solar arrays, windows, casings, and fabrics.

Figure 1A:
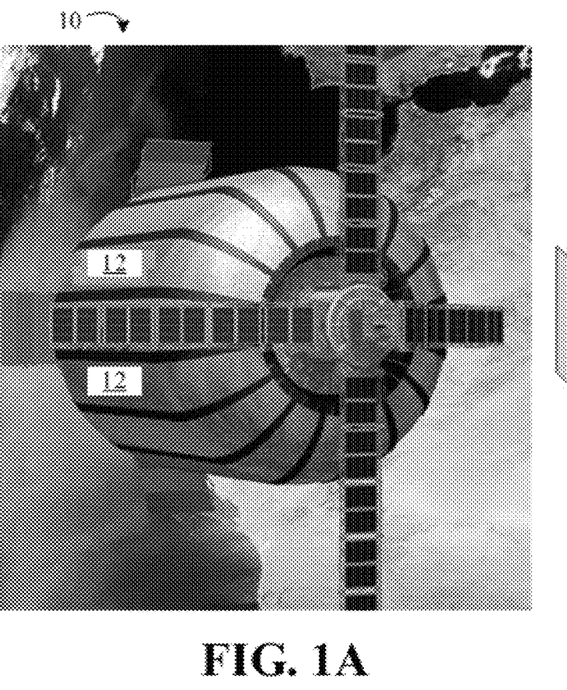
FIG. 1A is an illustration of an example of an inflatable spacecraft according an embodiment.
Figure 1B:
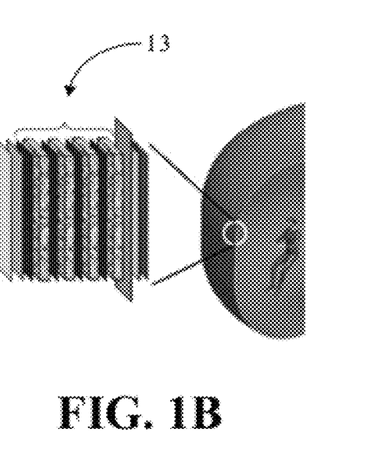
FIG. 1B is an exploded view of an example of a layered shell of an inflatable habitat according to an embodiment.

FIG. 1A illustrates an inflatable spacecraft 10 including an exterior structure that may be susceptible to damage from debris during launch, orbit, and/or landing. Accordingly, the exterior structure of the spacecraft 10 may be fabricated from a plurality of interconnected panels 12, wherein each panel 12 has a plurality of detection layers separated from one another by one or more detection layers. As will be discussed in greater detail, the plurality of detection layers can form a grid of conductive traces that may be monitored for electrical property changes. The detection of such electrical property changes can enable advanced damage detection activities such as the generation of diagnostic and/or prognostic outputs with respect to the exterior structure of the inflatable spacecraft 10. Wherein the outputs can identify damage to individual panels 12 via a spatially oriented or globally positioned coordinate system with respect to the inflatable spacecraft 10. Furthermore, the specific damage site locations on said individual panels 12 are determined by said panel's grid of conductive traces. FIG. 1B demonstrates that the outer shell/structure of a space habitat may include multiple layers.

Figure 2:
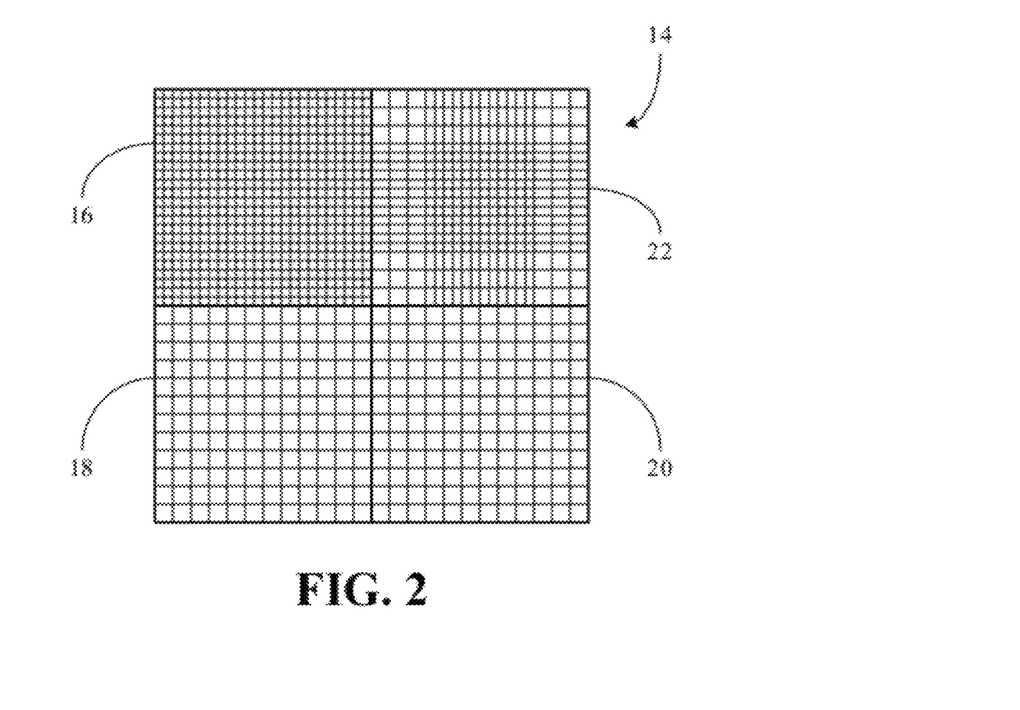
FIG. 2 is a diagram of an example of a detection pattern defined by a grid of conductive traces according to an embodiment.

FIG. 2 shows a detection pattern 14 that might be defined by a multi-layer grid of conductive traces. Several detection layers can be implemented, where alternate layers are arranged in an orthogonal direction with respect to adjacent layers. The orthogonal arrangement allows for pinpointing the exact location of the damage to the surface of the structure. Moreover, multiple detection layers allow for the calculation of the depth of the damage to the surface. Indeed, each detection layer may also include multiple known defect traces to facilitate panel identification as well as damage zone determination, as will be discussed in greater detail. The illustrated detection pattern 14 demonstrates that conductive traces of successive detection layers may be arranged perpendicular or angled to one another in order to provide the desired detection grid. For example, a first panel 16 has a detection pattern with a relatively high resolution, wherein a second panel 18 and a third panel 20 have a relatively low resolution. Thus, the first panel 16 could be used in areas of an exterior structure that are particularly susceptible to damage (e.g., sensitive launch and/or landing areas) or encompass particularly sensitive components of the spacecraft (e.g., navigational components, power supply, etc.). Moreover, each of the first three panels 16, 18, 20 also has a uniform resolution in the example shown. A fourth panel 22, on the other hand, might have a non-uniform resolution, which may be used to target even smaller areas for heightened detection sensitivity. In one example, traces are 0.020-inches thick and separated from each other by 0.020 inches.

Figure 3A:
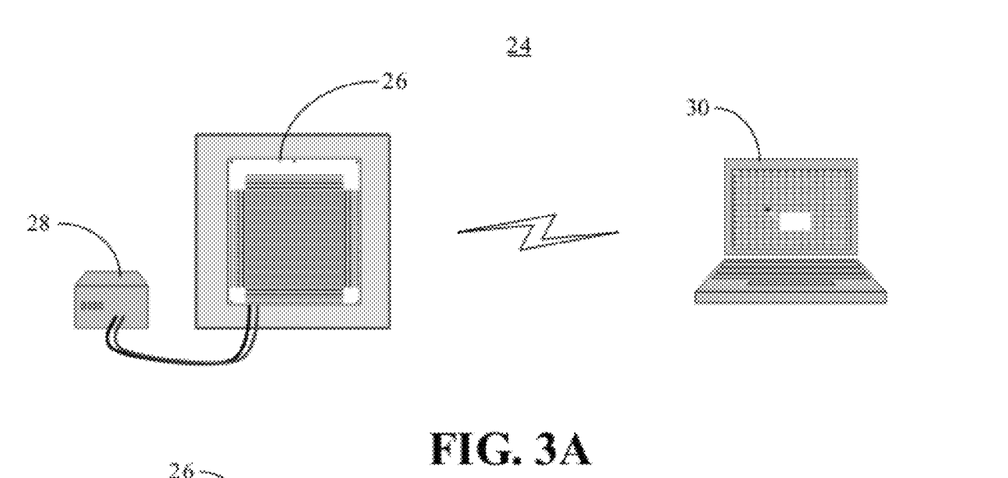
FIG. 3A is a diagram of an example of a detection system according to an embodiment.
Figure 3B:
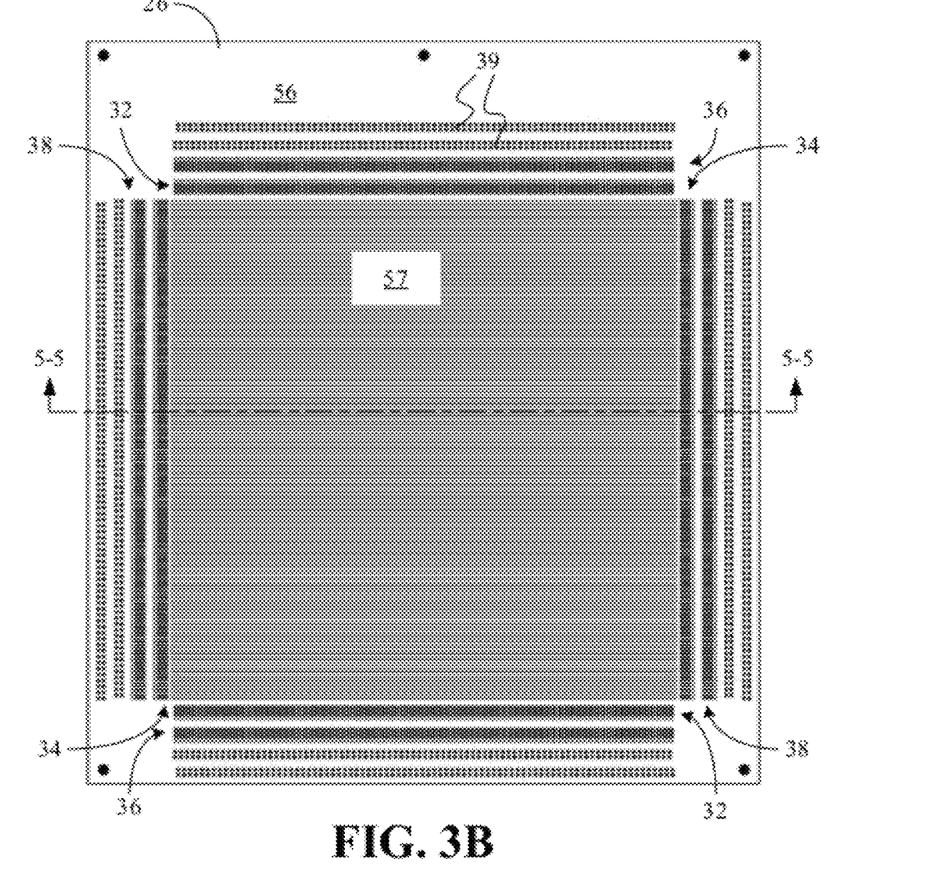
FIG. 3B is an enlarged view of an example of the detection panel assembly shown in FIG. 3A.

FIGS. 3A and 3B illustrate a multi-dimensional detection system 24, wherein the system 24 generally includes a multi-layered panel assembly 26 with a sensing panel 57 that is powered by a power supply 28 and communicatively coupled to a monitor 30. In some embodiments the monitor 30 may be a computer monitoring device that can only receive commands and/or data. In other embodiments the monitor 30 may be a computer monitoring device that can send and receive commands and/or data. And in further embodiments the monitor 30 may be a microcontroller or microprocessor embedded within the multi-layered panel assembly 26. Wherein the damage detection data may be stored within the microcontroller or microprocessor for accessing at a later date for eventual download and viewing on an external device.

In one example, an organic inherently conductive polymer may be used as a damage detection layer. For example, polyaniline derivatives have been demonstrated to function well as a damage detection conductor in a thin-film coating configuration having several thicknesses. Moreover, polyaniline coatings on polyethylenephthalate (PET) and KAPTON-H have performed successfully for damage detection. In addition to polyaniline, carbon nanotube (CNT), metal nanoparticle inks, and combinations thereof, thin films produced in accordance with embodiments of the present invention may be employed as conductors in thin-film configurations.

In the illustrated multi-dimensional detection system 24, two-dimensional detection layers of thin film may be used to form a layered composite, with thicker, non-detection layers separating the detection layers from one another. The thin-film detection layers can be formed of materials having a conductive grid or striped pattern such as the pattern 14 (FIG. 2) already discussed. The conductive pattern may be applied by a variety of methods including, but not limited to, printing, plating, sputtering, solvent casting, photolithography, and etching.

In a preferred embodiment, thin, conductive patterns are printed on one or more of a wide variety of substrates using a standard inkjet printer with several conductive inks. The substrates include, but are not limited to, polyimides, fluoropolymers, vinyl polymers, cotton fabrics, paper, and NOMEX. In designing the detection system, the number of detection layers chosen may depend on the level of damage detection detail needed. The damage will result in a change in electrical properties in the grid of conductive traces which can be detected utilizing the monitor 30, which may comprise a time domain reflectometer, resistivity monitoring hardware, capacitive measurement components, or other resistance-based detection systems. More particularly, the multi-dimensional damage detection system 24 can include a multiplicity of non-detection layers separated from one another by a multiplicity of detection layers, with each of the detection layers being connected to the monitor 30 in order to provide details regarding the physical health of each individual detection layer. If damage occurs to any of the detection layers, a change in the electrical properties of the damaged detection layer(s) may also occur, and a response may be generated. For example, real-time analysis of the responses may provide details regarding the depth and location of the damage. Moreover, multiple damage locations can be detected, and the extent (e.g., depth) of each damaged area can result in the generation of prognostic information related to the expected lifetime of the layered composite system.

The illustrated detection system 24 can be easily fabricated using commercial off-the-shelf (COTS) equipment and the detection algorithms may be updated as needed to provide the level of detail needed based on the system being monitored. Connecting the monitor 30 to the thin-film detection layers of the panel assembly 26 may provide a method of monitoring any damage that may occur.

For example, the monitor 30 can systematically output a test signal to the panel assembly 26 and manipulate the input data to determine a conclusion, wherein damaged trace/line and defect line numbers may be sorted in ascending order and then grouped into individual data arrays according to layer. The arrays may also be normalized so that each line number is referenced from a particular range (e.g., 0-167). Once the damaged and defect line numbers have been normalized, the monitor 30 may calculate the damaged line-number-to-line-number spacing. Damaged line numbers that occur sequentially can be grouped together to form a damage zone. The damage zone size may be calculated by determining the number of sequential lines found.

Once the damage zone size is calculated, the monitor 30 may resolve the appropriate defect analysis state to execute. In order to resolve the execution state, the monitor 30 may assume that the damage occurs on the panel assembly top (i.e., outer) layer and traverses through each subsequent layer. If damage does not occur on the top layer first, but rather on the inner layers only, the monitor 30 may reject and not process the data.

In one example, the monitor 30 utilizes a state machine with five states, wherein each state represents the number of layers of damage detected plus an idle state. The damage occurs in the proper order for the correct state to be performed. For example, if the embedded monitoring system reports that damage occurred on only the top layer and the bottom layer, then the state performed is State 1. In such a case, the data from the bottom layer may be ignored.

State 0—Idle, default, no data is processed
State 1—Damage detected on top layer only
State 2—Damage detected on the top two layers (1 & 2)

State 3—Damage detected on the top three layers (1, 2, & 3)

State 4—Damage detected on all four layers

Damage detected on the top layer only may be the easiest to process. In such a case, the monitor 30 can calculate the x-coordinate based on the normalized damaged line number multiplied by the spatial resolution of the grid (e.g., 0.04 inches). The y-coordinate may be set to zero because it is unknown since the damage did not penetrate to the second layer. The monitor 30 may complete its operation by populating a damage attributes cluster array. When the software detects that the y-coordinate is equal to zero in the cluster array, it can automatically draw a vertical color-coded line on the chart display object.

If damage is detected on two or more subsequent panel assembly layers, then the monitor 30 may begin a series of operations to determine the appropriate generalized scenario for each state. There are numerous lower-level cases that occur in each generalized scenario.

The following scenarios might be calculated for States 2-4.

Scenario #1: Damage Zone Array Sizes Equal 1

Since one damage zone is detected, the monitor 30 may pair the layer one damaged line numbers (x-coordinates) to the layer two damaged line numbers (y-coordinates) to form a coordinate pair. Since the damaged line numbers are sorted in ascending order, the lowest-value damaged line number in layer one (x) is paired to the lowest-value damaged line number in layer two (y). If the damage is symmetrical, the operator will observe on the chart graphic display object resolved color-coded points corresponding to damage depth layer; otherwise, whichever direction the number of damaged lines is greater (x or y) then vertical or horizontal lines will appear to represent the extra broken sensing lines that could not be paired. The monitor 30 can complete its operation by populating the damaged attributes cluster array.

Scenario #2: Damage Zone Array Sizes Are Equal but Greater Than 1

This scenario may occur for two reasons. First, multiple damage zones could be detected, which might happen when damage occurs simultaneously at different spots on the panel assembly (i.e., micrometeoroid shower). The second reason has to do with known defect lines. Damaged line numbers that occur sequentially are grouped together to form a damage zone. A single damage zone can appear to be multiple damage zones if there are defect lines that occur between a damaged line number sequence, causing the pattern to not be sequential. In this case, the monitor 30 determines if there are defects found in the zone, and if so, the damage zone size may be incremented based on the number of defects found. The monitor 30 can complete its operation by populating the damaged attributes cluster array.

Scenario #3: Damage Zone Array Sizes Are NOT Equal

This scenario may occur for two reasons. First, multiple damage zones may be detected, which can happen when damage occurs simultaneously at different spots on the panel assembly (e.g., micrometeoroid shower). In this particular scenario though, multiple damage zones may have been detected on the top layer, while on layer two, there were fewer damage zones detected because all the damage detected on the top layer didn't penetrate evenly through the panel assembly. Therefore, the damage zone array sizes might not be equal. If this is the reason, then the damaged line numbers from each layer might not be resolvable because there may be insufficient information to say for certain the location. Therefore, color-coded vertical and/or horizontal lines could be drawn to represent the broken sensing lines. In such a case, the operator may generally know the damage area, but not necessarily the exact location.

The second reason has to do with known defect lines (e.g., trace continuity signature information). Damaged line numbers that occur sequentially can be grouped together to form a damage zone, as already discussed. A single damage zone can appear to be multiple damage zones if there are defect lines that occur between a damaged line number sequence, causing the pattern not to be sequential. In this case, the monitor 30 may determine if there are defects found in the zone, and if so, the damage zone size can be incremented based on the number of defects found. There is a special scenario for the defects case. If two damage zones occurred simultaneously and one of those zones penetrated an area containing known defect traces and the other zone didn't contain known defect traces, the monitor 30 may have sufficient information to resolve the damage location and assign the appropriate x- and y-coordinates. If two damage zones exist and both have known defect traces or more than two damage zones exist, the algorithm may be unable to resolve the location and color-coded vertical and/or horizontal lines can be drawn to represent the broken sensing lines. Again, the monitor 30 may complete its operation by populating the damaged attributes cluster array.

After the generalized scenarios have been executed and the damaged attributes cluster array have been populated with the most current information, the illustrated monitor 30 plots the damaged attributes cluster array data on a graphic chart display object. If either x- or y-coordinate pair equals 0, then a color-coded vertical or horizontal line may be plotted rather than a point, wherein the line or point fill color may be determined by a damage depth layer value in the damaged attributes cluster array. For example, the layer damage color code could be defined as below.

Top Layer=white
Second Layer=blue
Third Layer=yellow
Bottom Layer=red

In the illustrated example, a first plurality of inside conductive pads 34 facilitate electrical connection to the conductive traces (e.g., horizontally arranged) of a first detection layer, and a second plurality of inside conductive pads 32 facilitate electrical connection to the conductive traces (vertically arranged) of a second detection layer. Where inside conductive pads 32 and 34 may be configured perpendicular to each other. Similarly, a first plurality of outside conductive pads 38 may facilitate electrical connection to the conductive traces (horizontally arranged) of a third detection layer, and a second plurality of outside conductive pads 36 can facilitate electrical connection to the conductive traces (vertically arranged) of a fourth detection layer. Where outside conductive pads 36 and 38 may be configured perpendicular to each other. The inside conductive pads 32, 34 and the outside conductive pads 36, 38, which may be disposed on a circuit substrate 56 adjacent to the perimeter of the panel assembly 26, can be used to interconnect panels with one another or to connect panels to the monitor 30. Indeed, the monitor 30 may be coupled to the grid of conductive traces via a wireless link (e.g., Bluetooth or Wi-Fi) or a wired link, and may even be embedded into the panel assembly 26 itself. In one example, such an embedded monitoring system is capable of monitoring the health of hundreds of sensing lines and reporting their status within seconds. Moreover, conductive traces of successive detection layers may be arranged substantially perpendicular to one another in order to achieve the desired detection grid, as already discussed.

Thus, a total of 28 data traces/lines from a microcontroller of the monitor 30 might be used to inject test signals into the parallel conductors in the detection layers, and a total of 24 data lines may be used to monitor the presence of the test signals at the opposite ends. A series of diodes 39 can also used to isolate the lines in the detection layers from each other in order to be able to evaluate the condition of each line independently of the condition of other lines. The test signal may be composed of a sequence of digital ones and zeros (e.g., binary pattern) and can be applied to one end of each line, wherein the signal at the opposite end may be monitored to determine the presence or absence of the test signal.

The monitor 30 at the end of each line may expect to see the binary pattern in order to make a determination that the integrity of the line under test has not been compromised, wherein deviations from the expected pattern may indicate that damage has occurred. In one example, a connection may be made at the cathode of each isolation diode 39 downstream from the monitor 30. If the peak voltage is above the complementary metal oxide semiconductor (CMOS) logic threshold level that signifies a digital "high" or "one," the trace may be considered a good (i.e., undamaged) line. Such an approach can enable detection of damaged lines that are not completely broken (e.g., have a resistance that is high enough to drop the voltage level below the logic threshold). Once a failure has been detected, the line number information may be stored in non-volatile memory to allow for it to be used as a baseline of information related to existing damage. The non-volatile flash memory can provide the capability to store hundreds (e.g., 256) of broken lines or damage identifier (ID) information. The maximum historical data that can be stored may be based on a 5-bit damage ID number and a 10-bit damage line number value. Storing the information in this format may be very efficient and can involve a relatively small memory footprint.

Figure 4:
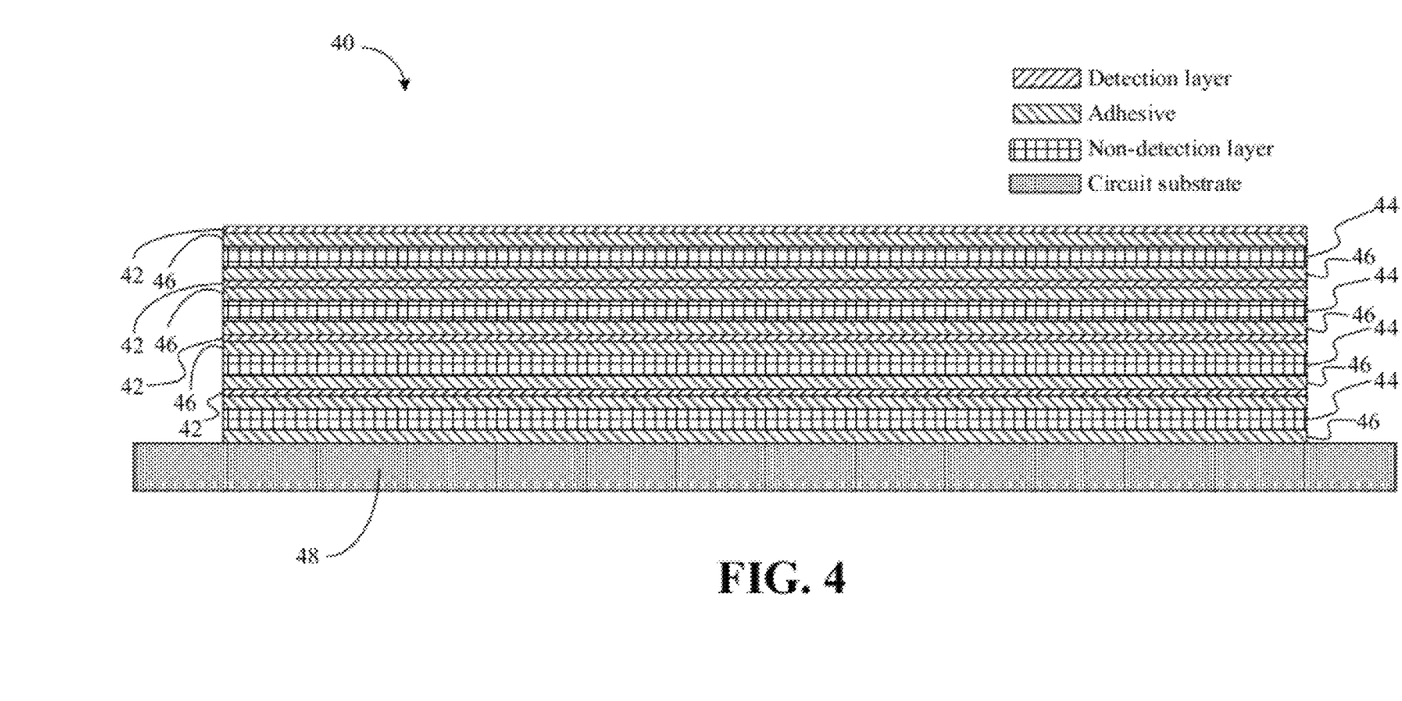
FIG. 4 is a sectional view of an example of a plurality of detection layers according to an embodiment.

FIG. 4 shows a sectional view of a detection panel 40 having a plurality of detection layers 42 separated from one another by one or more non-detection layers 44. In particular, each detection layer 42 may include a film substrate and a plurality of conductive traces coupled to the film substrate, as already discussed. Moreover, the conductive traces of successive detection layers can be substantially perpendicular to one another in either a uniform or non-uniform resolution/configuration. In the illustrated example, adhesive layers 46 are used as an interface between successive detection and non-detection layers. A circuit substrate 48 may also be coupled to an outside layer of the panel 40, wherein the circuit substrate 48 may be constructed of a flexible and/or rigid material. Of particular note is that a flexible circuit substrate 48 may be particularly advantageous for inflatable platform structure applications.

Figure 5:
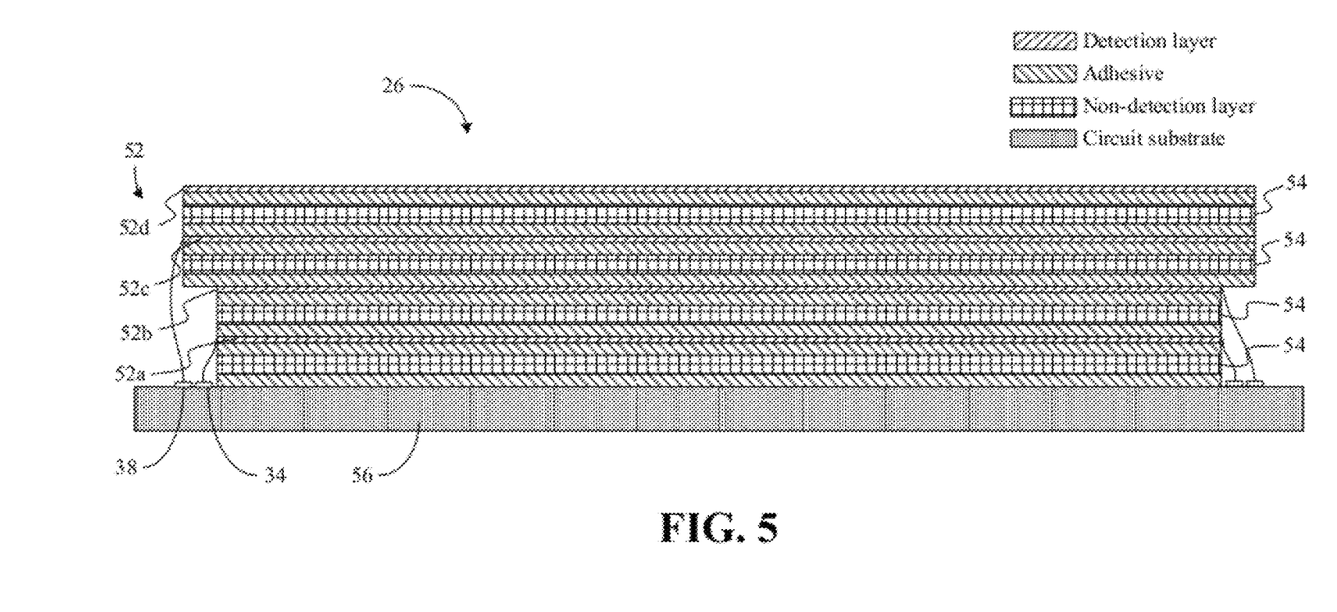
FIG. 5 is a sectional view taken along lines 5-5 of FIG. 3 according to an embodiment.

FIG. 5 illustrates a sectional view of the aforementioned detection panel assembly 26, wherein the illustrated detection panel assembly 26 has a panel with a staggered profile to enhance connectivity. In the illustrated example, a plurality of detection layers 52 (52a-52d) are separated from one another by a plurality of non-detection layers 54. The horizontally arranged conductive traces of the bottom (e.g., first) detection layer 52a can be connected to one or more inside conductive pads 34, whereas the vertically arranged (into the page) conductive traces of the next (e.g., second) detection layer 52b may be connected to one or more inside conductive pads 32 (FIG. 3B). Similarly, the horizontally arranged conductive traces of the next (e.g., third) detection layer 52c can be connected to one or more outside conductive pads 38, whereas the vertically arranged (into the page) conductive traces of the top (e.g., fourth) detection layer 52d may be connected to one or more outside conductive pads 36 (FIG. 3B). The conductive traces of the upper set of detection layers 52c, 52d, may have a wider profile in order to provide greater clearance and facilitate connection to the outside conductive pads 38, 36, respectively. The illustrated conductive pads 34, 38 are mounted to a circuit substrate 56, which is also coupled to an outside layer of the panel assembly 26, in the example shown.

To ensure good electrical continuity between the flexible sensing panel and the printed circuit board 56, a mounting frame (or compression ring, not shown) may be used to apply even compression and proper alignment of the sensing panel to the circuit board 56. Alignment dowels can be included in the printed circuit board assembly, wherein the flexible sensing panels may have corresponding holes that enable proper alignment and prevents panel slippage. In one example, the compression ring is made of polycarbonate and has a 6-inch by 6-inch opening in the center to allow the active area of the sensing panel to be fully exposed. The compression ring may attach to a back plate behind the circuit board with screws. The screws can pass through holes in the compression ring, one at each corner and three along each side, and corresponding holes in the circuit board, then thread into helicoils in the back plate. When the screws are tightened, the ring can bias/press the sensing panel against the circuit board 56 and secure it in place.

On the bottom side of the compression ring, covering the portion of the circuit board which has the pads, there may be a gasket (e.g., buna-n-rubber). The gasket provides a tight fit against the sensing panel that both ensures good contact and keeps the circuit board 56 and other components from being exposed to the elements.

Figure 6:
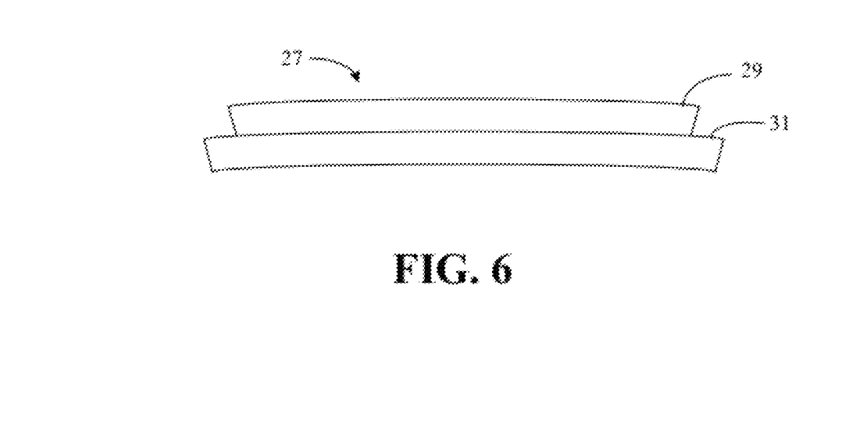
FIG. 6 is a side view of an example of a flexible detection panel assembly according to an embodiment.

FIG. 6 shows a flexible panel assembly 27. The illustrated panel assembly 27 includes a multilayered flexible panel 29 coupled to a flexible circuit board 31. The panel assembly 27 may also include a microcontroller, custom firmware, bidirectional serial port driver, and diodes for electrical isolation. In addition, the panel assembly 27 could include wired/wireless network capability or the entire assembly 27 could be fabricated from a rigid-flexible printed circuit board.

Figure 7:
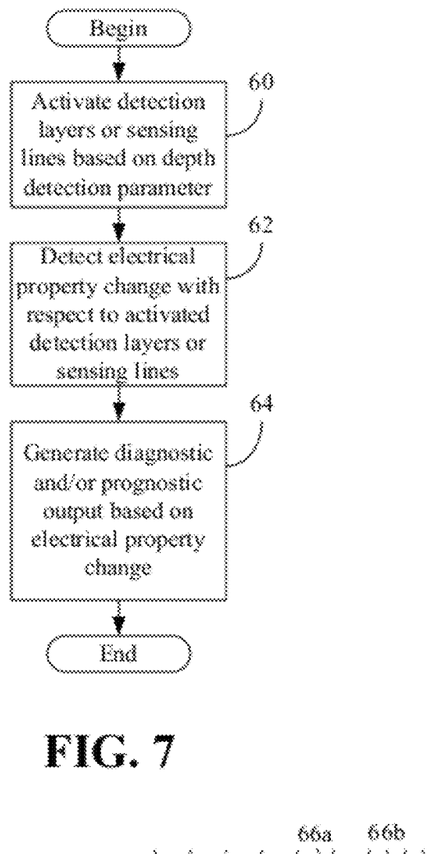
FIG. 7 is a flowchart of an example of a method of evaluating a structure according to an embodiment.

FIG. 7 shows a method 58 of evaluating a structure. The method 58 may be implemented as hardware, firmware, software (e.g., LabVIEW), or any combination thereof, in a monitor such as the monitor 30 (FIG. 3A), already discussed. Illustrated processing block 60 provides for selectively deactivating one or more of a plurality of detection layers or sensing lines in a plurality of interconnected panels based on a depth detection parameter. For example, block 60 could involve deactivating (e.g., masking) the conductive traces of the first detection layer 52a (FIG. 5) so that damage to only approximately three fourths of the overall thickness of a given panel would be detected. An electrical property change with respect to the activated detection layers may be detected at block 62, wherein block 64 can generate one or more of a diagnostic output and a prognostic output based on the electrical property change. In one example, a graphical user interface (GUI, e.g., written in LabVIEW) is used to communicate the detection results to various personnel via the monitor 30 (FIG. 3A).

Figure 8:
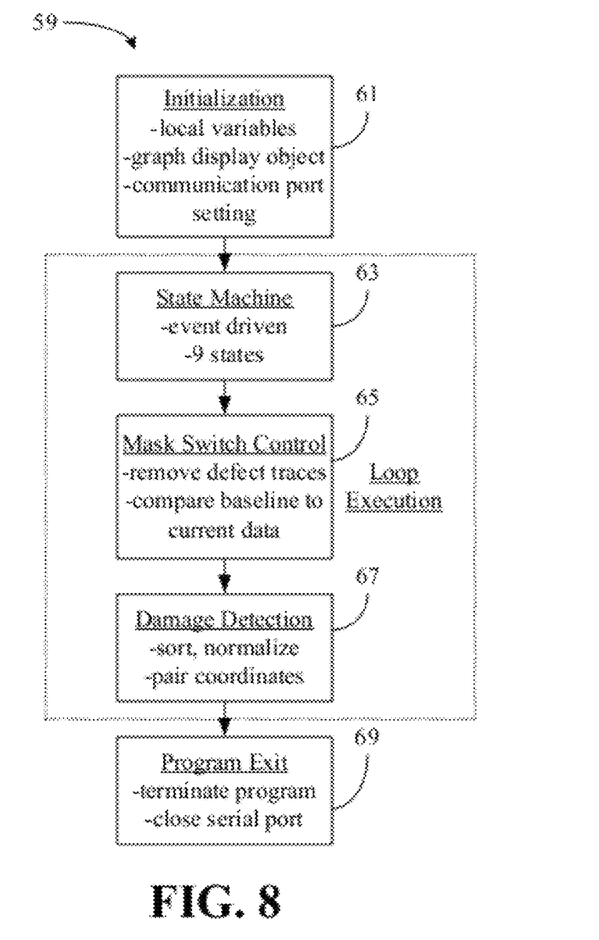
FIG. 8 is a flowchart of an example of a method of detecting damage according to an embodiment.

FIG. 8 shows a method 59 of detecting damage in greater detail. Illustrated processing block 61 provides for initialization of local variables, graph display objects (e.g., X and Y axes; grid), and communication settings, wherein a state machine can be invoked at block 63. In the illustrated example, the state machine is event driven and supports up to nine different states. Block 65 may conduct mask switch control in order to remove known defect traces and compare baseline data to current data. A damage detection software algorithm or subroutine may be invoked at block 67, wherein the damage detection software algorithm or subroutine sorts and normalizes damaged trace identifiers, as well as pairs coordinate values, in the example shown. Blocks 63, 65, and 67 may be executed in a loop on a periodic basis (e.g., every 100 ms). Illustrated block 69 provides for exiting the program and closing communication ports.

Thus, software may interpret the damage line numbers detected by a microcontroller and sort and organize the individual damaged sensing lines into damage zones with location and depth. In one example, there are two types of software—GUI software and firmware. The firmware, which may be stored in non-volatile memory in the microcontroller, can monitor the individual sensing lines by sending out a test signal sequentially on each line. It may also store historical data regarding the damage ID and damage line numbers and transmit that data to the GUI when requested. During normal operation, the microcontroller outputs a test sequence composed of alternating ones and zeros. At the same time, the microcontroller determines the response of the grid of conductive traces to the test sequence and determines whether the correct pattern has been received or not. The integrity of a line in the detection layer may be deemed to be good (i.e., undamaged) if the received pattern is identical to the transmitted pattern. The process may then be repeated for all traces. The microcontroller can also be programmed to listen for commands coming from a host computer. These commands can be used to request specific functions from the board, including real-time retrieval of data, baselining of existing damages, and auto-loop or single scan mode of operation.

Figure 9:
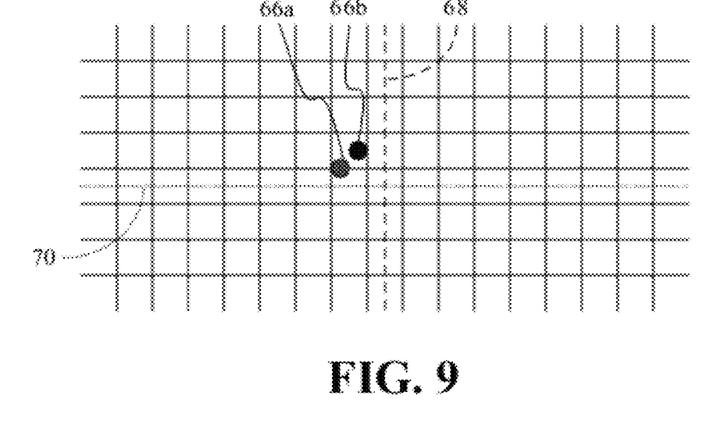
FIG. 9 is an illustration of an example of a graphical user interface (GUI) according to an embodiment.

FIG. 9 illustrates a GUI in which panel damage is characterized for users. In the illustrated example, multiple points 66 (66a, 66b) are drawn against a pattern reflecting a grid of conductive traces, wherein the points represent collective damage to the traces of the grid (e.g., a damage zone). The points 66 may be drawn differently to reflect damage depth (e.g., the deepest layer damaged). For example, the designed point 66a could indicate that damage has been detected down to the third deepest layer, whereas the solid point 66b might indicate that damage has been detected down to the fourth deepest layer. In such a case, the user may be able to readily ascertain an angle of incidence to the impacted panel as well as the level of severity. Other differentiators such as color and/or size may also be used for the points 66. Moreover, the points 66 can be used to determine damage area.

Additionally, the GUI may be used to indicate particular traces that have been damaged (e.g., where damage pinpointing is not available). In the illustrated example, a vertical line 68 is drawn to reflect damage to a vertically arranged trace, and a horizontal line 70 is drawn to reflect damage to a horizontally arranged trace. The lines 68, 70 may also be drawn differently to reflect damage depth. For example, the dash frequency of the vertical line 68 could indicate that damage occurred in the second deepest layer, whereas the dash frequency of the horizontal line could reflect that damage occurred in the shallowest layer. Other differentiators such as color and/or size may also be used for the points 66.

Implementation Example

The system can include three main custom designed subsystems: a four-layer KAPTON sensing panel with mounting frame, an embedded monitoring system, and a graphical user interface (GUI). The sensing panel may include four monitoring layers perpendicular to each other creating a three-dimensional grid pattern. Each layer may include a KAPTON sheet printed with 168 parallel conductive ink traces 20-mils wide with a trace-to-trace spacing of 20 mils. KEVLAR fabric can be sandwiched between each sheet and glued together with adhesive to form the sensing panel. A mounting frame can align and mount the sensing panel to the embedded monitoring system.

The system may determine the identification number of the sensing panel by utilizing either the first four or the last four conductive traces on each of the individual layers. This is accomplished by creating known patterns of breaks in the electrical continuity of these traces and scanning the traces for continuity. For example, if the first four traces of a layer are used (4 bits), up to 16 different combinations (e.g., trace continuity signatures) can be generated, providing the capability to identify up to 16 unique panels. Additional conductive traces can be utilized on the other layers to increase the total number of unique panels that can be identified.

The embedded monitoring system may include a printed circuit board that interfaces with the sensing panel. Additionally, a microcontroller or microprocessor may actively monitor the health of all 672 traces (4×168) and report status information to the GUI software. Flash memory can be used to store an ID and the damaged line numbers associated with each ID number. The on-board memory may be used to log historical data, thus allowing the reconstruction of the damage events at a later date. Knowledge of the sequence of damage events and which sensing lines were broken for each event can enable the GUI software to sort and accurately assign a damage location. The microcontroller status may be wirelessly (e.g., up to 100 meters) reported to a laptop running the GUI, wherein the GUI software may be written in LabVIEW and can use a custom developed damage detection algorithm to determine the damage location based on the sequence of broken sensing lines. The algorithm may estimate the damage size and maximum depth, and also plot the damage location on a graph to be viewed on a computer monitor or other graphics device.

The GUI software may utilize scripting to enable either autonomous or manual operation of the system. This allows for a single GUI to be utilized for multiple operational scenarios, making the system more versatile. Script files may contain other information related to operational mode (autonomous or manual), data sampling rate, time stamp, method of data transmission (e.g., wireless, Bluetooth, serial, Ethernet, Wi-Fi, etc.), and operational tasks (e.g., read baseline, determine panel identification number, load mask file, erase baseline, etc.). The script file can be modified and specifically tailored, as needed, to provide the most efficient operation of the system for a given application.

Integrated testing included drilling holes of various diameters, shapes, and sizes at different depths into the sensing panel and verifying the functionality of both the embedded systems and the GUI software. The holes emulated the potential damage which can be caused by micrometeorites or other space debris impacting the habitat's exterior surface.

Preferred embodiments may therefore include an apparatus having a panel with a plurality of detection layers separated from one another by one or more non-detection layers, wherein the plurality of detection layers form a grid of conductive traces. The apparatus can also have a monitor coupled to the grid of conductive traces, wherein the monitor is configured to detect damage to the pane in response to an electrical property change with respect to one or more of the conductive traces.

Other preferred embodiments may also include a system having a platform such as an inflatable spacecraft or non-inflatable habitation structure with a plurality of interconnected panels, wherein each panel has a plurality of detection layers separated from one another by one or more non-detection layers. The plurality of detection layers may form a grid of conductive traces. The system can also have a monitor coupled to each grid of conductive traces, wherein the monitor is configured to detect damage to the plurality of interconnected panels in response to an electrical property change with respect to one or more of the conductive traces.

Embodiments may also include a method in which a test signal is transmitted to a plurality of interconnected panels, wherein each panel has a plurality of detection layers that form a grid of conductive traces. The method can also provide for identifying one or more damage zones in the plurality of interconnected panels based on a response of the grid of conductive traces to the test signal and trace continuity signature information associated with the plurality of interconnected panels.

Moreover, embodiments can include a computer readable storage medium having a set of instructions which, if executed by a processor, cause a computer to transmit a test signal to a plurality of interconnected panels, wherein each panel has a plurality of detection layers that form a grid of conductive traces. The instructions, if executed, may also cause a computer to identify one or more damage zones in the plurality of interconnected panels based on a response of the grid of conductive traces to the test signal and trace continuity signature information associated with the plurality of interconnected panels.

Additionally, embodiments may include a method of fabricating an inflatable spacecraft or habitation in which a plurality of panels are provided as an exterior structure of the inflatable spacecraft. Each panel can have a plurality of detection layers separated from one another by one or more non-detection layers, wherein each detection layer includes a film substrate and a plurality of conductive traces coupled to the film substrate. Moreover, conductive traces of successive detection layers may be substantially perpendicular to one another, wherein the plurality of detection layers form a grid of conductive traces. The method can also involve interconnecting the plurality of panels, and configuring a monitor to selectively deactivate (e.g., mask) one or more of the plurality of detection layers or sensing lines based on a depth detection parameter. The monitor may also be configured to detect damage to the plurality of panels in response to an electrical property change with respect to one or more of the conductive traces, and generate one or more of a diagnostic output and a prognostic output based on the electrical property change. In addition, the method may include coupling the monitor to the plurality of panels.

Thus, embodiments of the present invention can provide a unique multi-dimensional damage detection system that is completely flexible and can easily be designed to gather as much or as little information as the end user deems necessary. Additionally, individual detection layers can be turned on or off as needed and the controlling algorithms may be optimized as needed. Simply put, the illustrated systems can be used to generate both diagnostic and prognostic information related to the health of layered composite structures, which may be essential if such systems are utilized for space exploration and habitat.

The term "coupled" may be used herein to refer to any type of relationship, direct or indirect, between the components in question, and may apply to electrical, mechanical, fluid, optical, electromagnetic, electromechanical, or other connections. In addition, the terms "first," "second," etc. may be used herein only to facilitate discussion, and carry no particular temporal or chronological significance unless otherwise indicated.

Those of ordinary skill in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

We claim:

1. An apparatus comprising:
a panel including a plurality of detection layers, each detection layer including a substrate and a plurality of conductive traces coupled to the substrate, each detection layer separated from one another by one or more non-detection layers, wherein the plurality of detection layers form a grid of conductive traces and wherein each detection layer includes one or more known defect traces, and wherein the panel has a trace continuity signature that is defined by the known defect traces of the detection layers in the panel; and
a monitor coupled to the grid of conductive traces, wherein the monitor is configured to detect damage to the panel in response to an electrical property change with respect to one or more of the conductive traces.

2. The apparatus of claim 1, wherein conductive traces of successive detection layers are substantially perpendicular to one another.

3. The apparatus of claim 1, wherein the grid has a non-uniform resolution.

4. The apparatus of claim 1, wherein the monitor is configured to selectively deactivate one or more of the plurality of detection layers or sensing lines based on a depth detection parameter.

5. The apparatus of claim 1, wherein the monitor is configured to generate one or more of a diagnostic output and a prognostic output based on the electrical property change.

6. The apparatus of claim 1, further including a circuit substrate coupled to an outside layer of the panel.

7. The apparatus of claim 6, wherein the circuit substrate includes a plurality of inside conductive pads and a plurality of outside conductive pads disposed adjacent to a perimeter of the panel, and wherein the plurality of inside conductive pads and the plurality of outside conductive pads are electrically connected to the grid.

8. The apparatus of claim 1, wherein the monitoring system uses one or more script files to facilitate detection of the damage.

9. The apparatus of claim 1, further including a compression ring that biases the panel against the circuit board.

* * * * *